US011045583B2

(12) United States Patent
Jessop

(10) Patent No.: US 11,045,583 B2
(45) Date of Patent: Jun. 29, 2021

(54) DEVICES AND METHODS FOR TISSUE CRYOMILLING

(71) Applicant: LifeCell Corporation, Branchburg, NJ (US)

(72) Inventor: Israel James Jessop, Annandale, NJ (US)

(73) Assignee: LifeCell Corporation, Madison, NJ (US)

( * ) Notice: Subject to any disclaimer, the term of this patent is extended or adjusted under 35 U.S.C. 154(b) by 649 days.

(21) Appl. No.: 15/847,158

(22) Filed: Dec. 19, 2017

(65) Prior Publication Data

US 2018/0177919 A1     Jun. 28, 2018

Related U.S. Application Data

(60) Provisional application No. 62/438,241, filed on Dec. 22, 2016.

(51) Int. Cl.
| | | |
|---|---|---|
| G01N 1/00 | (2006.01) | |
| A61L 27/36 | (2006.01) | |
| F25D 31/00 | (2006.01) | |
| B26D 3/24 | (2006.01) | |
| A61L 27/50 | (2006.01) | |
| A61B 17/322 | (2006.01) | |
| B26D 7/01 | (2006.01) | |
| B26D 7/10 | (2006.01) | |

(52) U.S. Cl.
CPC ........ *A61L 27/3691* (2013.01); *A61B 17/322* (2013.01); *A61L 27/3604* (2013.01); *A61L 27/3683* (2013.01); *A61L 27/3695* (2013.01); *A61L 27/50* (2013.01); *B26D 3/24* (2013.01); *B26D 7/018* (2013.01); *B26D 7/10* (2013.01); *F25D 31/00* (2013.01); *A61B 2017/3225* (2013.01); *A61L 2400/08* (2013.01); *A61L 2400/18* (2013.01); *A61L 2430/34* (2013.01)

(58) Field of Classification Search
None
See application file for complete search history.

(56) References Cited

U.S. PATENT DOCUMENTS

| 4,582,640 A | 4/1986 | Smestad et al. |
| 4,902,508 A | 2/1990 | Badylak et al. |
(Continued)

FOREIGN PATENT DOCUMENTS

| JP | 2004-107303 A | 4/2004 |
| WO | 2003/017826 A2 | 3/2003 |
(Continued)

OTHER PUBLICATIONS

Ahn et al., The past, present, and future of xenotransplantation. Yonsei Med J. Dec. 31, 2004;45(6):1017-24.
(Continued)

*Primary Examiner* — Jyoti Nagpaul
(74) *Attorney, Agent, or Firm* — McCarter & English, LLP

(57) ABSTRACT

The present application relates to a method and device for processing tissue. The method and device allow for machining of soft tissue samples to produce uniform shapes (e.g., uniform thicknesses) or reliably produce alterations such as openings or holes in soft tissue products. The method and device can alternatively or additionally be used to process tissue to produce particulates with desired properties.

20 Claims, 7 Drawing Sheets

(56) References Cited

U.S. PATENT DOCUMENTS

| | | | |
|---|---|---|---|
| 4,969,912 A | 11/1990 | Kelman et al. |
| 5,104,957 A | 4/1992 | Kelman et al. |
| 5,131,850 A | 7/1992 | Brockbank |
| 5,160,313 A | 11/1992 | Carpenter et al. |
| 5,231,169 A | 7/1993 | Constantz et al. |
| 5,254,133 A | 10/1993 | Seid |
| 5,275,826 A | 1/1994 | Badylak et al. |
| 5,284,655 A | 2/1994 | Bogdansky et al. |
| 5,332,802 A | 7/1994 | Kelman et al. |
| 5,332,804 A | 7/1994 | Florkiewicz et al. |
| 5,336,616 A | 8/1994 | Livesey et al. |
| 5,364,756 A | 11/1994 | Livesey et al. |
| 5,489,304 A | 2/1996 | Orgill et al. |
| 5,547,681 A | 8/1996 | Clark et al. |
| 5,613,982 A | 3/1997 | Goldstein |
| 5,632,778 A | 5/1997 | Goldstein |
| 5,641,518 A | 6/1997 | Badylak et al. |
| 5,728,752 A | 3/1998 | Scopelianos et al. |
| 5,739,176 A | 4/1998 | Dunn et al. |
| 5,800,537 A | 9/1998 | Bell |
| 5,893,888 A | 4/1999 | Bell |
| 5,993,844 A | 11/1999 | Abraham et al. |
| 6,027,743 A | 2/2000 | Khouri et al. |
| 6,096,347 A | 8/2000 | Geddes et al. |
| 6,113,623 A | 9/2000 | Sgro |
| 6,166,288 A | 12/2000 | Diamond et al. |
| 6,179,872 B1 | 1/2001 | Bell et al. |
| 6,194,136 B1 | 2/2001 | Livesey et al. |
| 6,248,114 B1 | 6/2001 | Ysebaert |
| 6,326,018 B1 | 12/2001 | Gertzman et al. |
| 6,364,908 B1 | 4/2002 | Ysebaert |
| 6,371,992 B1 | 4/2002 | Tanagho et al. |
| 6,381,026 B1 | 4/2002 | Schiff et al. |
| 6,432,710 B1 | 8/2002 | Boss, Jr. et al. |
| 6,485,723 B1 | 11/2002 | Badylak et al. |
| 6,576,265 B1 | 6/2003 | Spievack |
| 6,666,892 B2 | 12/2003 | Hiles et al. |
| 6,835,385 B2 | 12/2004 | Buck |
| 6,933,326 B1 | 8/2005 | Griffey et al. |
| 7,358,284 B2 | 4/2008 | Griffey et al. |
| 7,425,322 B2 | 9/2008 | Cohn et al. |
| 7,498,040 B2 | 3/2009 | Masinaei et al. |
| 7,498,041 B2 | 3/2009 | Masinaei et al. |
| 7,521,021 B2 * | 4/2009 | McCormick ............ G01N 1/31 422/536 |
| 7,799,767 B2 | 9/2010 | Lamberti et al. |
| 7,838,021 B2 | 11/2010 | Lafont et al. |
| 8,067,149 B2 | 11/2011 | Livesey et al. |
| 8,257,372 B2 | 9/2012 | Swain et al. |
| 8,324,449 B2 | 12/2012 | McQuillan et al. |
| 9,206,442 B2 | 12/2015 | Chen |
| 9,238,793 B2 | 1/2016 | Chen et al. |
| 9,375,513 B2 | 6/2016 | Sun et al. |
| 9,382,422 B2 | 7/2016 | Owens et al. |
| 9,592,254 B2 | 3/2017 | Monteiro et al. |
| 9,594,004 B2 | 3/2017 | Fry et al. |
| 10,207,025 B2 | 2/2019 | Chen et al. |
| 2001/0029380 A1 | 10/2001 | Ysebaert |
| 2002/0103542 A1 | 8/2002 | Bilbo |
| 2003/0035843 A1 | 2/2003 | Livesey et al. |
| 2003/0143207 A1 | 7/2003 | Livesey et al. |
| 2004/0037735 A1 | 2/2004 | DePaula et al. |
| 2004/0191226 A1 | 9/2004 | Badylak |
| 2005/0028228 A1 | 2/2005 | McQuillan et al. |
| 2005/0159822 A1 | 7/2005 | Griffey et al. |
| 2006/0073592 A1 | 4/2006 | Sun et al. |
| 2006/0127375 A1 | 6/2006 | Livesey et al. |
| 2006/0159641 A1 | 7/2006 | Girardot et al. |
| 2006/0210960 A1 | 9/2006 | Livesey et al. |
| 2006/0272102 A1 | 12/2006 | Liu et al. |
| 2007/0009586 A1 | 1/2007 | Cohen et al. |
| 2007/0078522 A2 | 4/2007 | Griffey et al. |
| 2007/0104759 A1 | 5/2007 | Dunn et al. |
| 2007/0248575 A1 | 10/2007 | Connor et al. |
| 2008/0027542 A1 | 1/2008 | McQuillan et al. |
| 2008/0027562 A1 | 1/2008 | Fujisato et al. |
| 2009/0035289 A1 | 2/2009 | Wagner et al. |
| 2009/0130221 A1 | 5/2009 | Bolland et al. |
| 2009/0239809 A1 | 9/2009 | Chen et al. |
| 2009/0306790 A1 | 12/2009 | Sun |
| 2010/0021961 A1 | 1/2010 | Fujisato et al. |
| 2010/0040687 A1 | 2/2010 | Pedrozo et al. |
| 2010/0209408 A1 | 8/2010 | Stephen A. et al. |
| 2010/0233235 A1 | 9/2010 | Matheny et al. |
| 2010/0272782 A1 | 10/2010 | Owens et al. |
| 2011/0020271 A1 | 1/2011 | Niklason et al. |
| 2011/0021753 A1 | 1/2011 | Huang |
| 2012/0010728 A1 | 1/2012 | Sun et al. |
| 2012/0040013 A1 | 2/2012 | Owens et al. |
| 2012/0252065 A1 | 10/2012 | Rozenszain et al. |
| 2012/0263763 A1 | 10/2012 | Sun et al. |
| 2012/0276213 A1 | 11/2012 | Chen |
| 2012/0310367 A1 | 12/2012 | Connor |
| 2013/0013068 A1 | 1/2013 | Forsell et al. |
| 2013/0053960 A1 | 2/2013 | Park et al. |
| 2013/0121970 A1 | 5/2013 | Owens et al. |
| 2013/0158676 A1 | 6/2013 | Hayzlett et al. |
| 2014/0004549 A1 | 1/2014 | Chen et al. |
| 2015/0105669 A1 | 4/2015 | Rovira et al. |
| 2015/0197030 A1 | 7/2015 | Fry et al. |
| 2016/0271295 A1 | 9/2016 | Sun et al. |
| 2017/0209619 A1 | 7/2017 | Monteiro et al. |
| 2017/0212014 A1 | 7/2017 | Fry et al. |
| 2019/0076582 A1 | 3/2019 | Connor |

FOREIGN PATENT DOCUMENTS

| | | |
|---|---|---|
| WO | 2003/032735 A1 | 4/2003 |
| WO | 2009/009620 A2 | 1/2009 |
| WO | 2010/078353 A2 | 7/2010 |

OTHER PUBLICATIONS

Allman et al., Xenogeneic extracellular matrix grafts elicit a TH2-restricted immune response. Transplantation. Jun. 15, 2001;71(11):1631-40.

Aycock et al., Parastomal hernia repair with acellular dermal matrix. J Wound Ostomy Continence Nurs. Sep.-Oct. 2007;34(5):521-3.

Badylak et al., Endothelial cell adherence to small intestinal submucosa: an acellular bioscaffold. Biomaterials. Dec. 1999;20(23-24):2257-63.

Badylak et al., Extracellular matrix as a biological scaffold material: Structure and function. Acta Biomater. Jan. 2009;5(1):1-13.

Beniker et al., The use of acellular dermal matrix as a scaffold for periosteum replacement. Orthopedics. May 2003;26(5 Suppl):s591-6.

Bruder et al., The effect of implants loaded with autologous mesenchymal stem cells on the healing of canine segmental bone defects. J Bone Joint Surg Am. Jul. 1998;80(7):985-96.

Buma et al., Tissue engineering of the meniscus. Biomaterials. Apr. 2004;25(9):1523-32.

Chaplin et al., Use of an acellular dermal allograft for dural replacement: an experimental study. Neurosurgery. Aug. 1999;45(2):320-7.

Chen et al., Acellular collagen matrix as a possible "off the shelf" biomaterial for urethral repair. Urology. Sep. 1999;54(3):407-10.

Collins et al., Cardiac xenografts between primate species provide evidence for the importance of the alpha-galactosyl determinant in hyperacute rejection. J Immunol. May 15, 1995;154(10):5500-10.

Costantino et al., Human dural replacement with acellular dermis: clinical results and a review of the literature. Head Neck. Dec. 2000;22(8):765-71.

Dobrin et al., Elastase, collagenase, and the biaxial elastic properties of dog carotid artery. Am J Physiol. Jul. 1984;247(1 Pt 2):H124-31.

Edel, The use of a connective tissue graft for closure over an immediate implant covered with occlusive membrane. Clin Oral Implants Res. Mar. 1995;6(1):60-5.

Fowler et al., Ridge Preservation Utilizing an Acellular Dermal Allograft and Demineralized Freeze-Dried Bone Allograft: Part II. Immediate Endosseous Impact Placement. J Periodontol. Aug. 2000;71(8):1360-1364.

(56) References Cited

OTHER PUBLICATIONS

Fowler et al., Root coverage with an acellular dermal allograft: a three-month case report. J Contemp Dent Pract. Aug. 15, 2000;1(3):47-59.

Galie et al., Simultaneous application of interstitial flow and cyclic mechanical strain to a three-dimensional cell-seeded hydrogel. Tissue Eng Part C Methods. May 2011;17(5):527-36.

Galili et al., Interaction between human natural anti-alpha-galactosyl immunoglobulin G and bacteria of the human flora. Infect Immun. Jul. 1988:56(7):1730-7.

Galli et al., Man, apes, and Old World monkeys differ from other mammals in the expression of alpha-galactosyl epitopes on nucleated cells. J Biol Chem. Nov. 25, 1988;263(33):17755-62.

Galli, Interaction of the natural anti-Gal antibody with alpha-galactosyl epitopes: a major obstacle for xenotransplantation in humans. Immunol Today. Oct. 1993;14(10):480-2.

Gamba et al., Experimental abdominal wall defect repaired with acellular matrix. Pediatr Surg Int. Sep. 2002;18(5-6):327-31.

Gebhart et al., A radiographical and biomechanical study of demineralized bone matrix implanted into a bone defect of rat femurs with and without bone marrow. Acta Orthop Belg. 1991;57(2):130-43.

Greenstein et al., Parastomal hernia repair using cross-linked porcine dermis: report of a case. Surg Today. 2008;38(11):1048-51.

Griffey et al., Particulate dermal matrix as an injectable soft tissue replacement material. J Biomed Mater Res. 2001;58(1):10-5.

Hamadeh et al., Human natural anti-Gal IgG regulates alternative complement pathway activation on bacterial surfaces. J Clin Invest. Apr. 1992;89(4):1223-35.

Harris, A comparative study of root coverage obtained with an acellular dermal matrix versus a connective tissue graft: results of 107 recession defects in 50 consecutively treated patients. Int J Periodontics Restorative Dent. Feb. 2000;20(1):51-9.

Harris, Root coverage with a connective tissue with partial thickness double pedicle graft and an acellular dermal matrix graft: a clinical and histological evaluation of a case report. J Periodontol. Nov. 1998;69(11):1305-11.

Ionescu et al., Effect of Papain and Bromelin on Muscle and Collagen Proteins in Beef Meat. The Annals of the University Dunarea de Jos of Galati. Fascicle VI, Food Technology, New Series, pp. 9-16, 2008.

Karlinsky et al., in vitro effects of elastase and collagenase on mechanical properties of hamster lungs. Chest. Feb. 1976;69(2 Suppl):275-6.

Kish et al., Acellular dermal matrix (AlloDerm): new material in the repair of stoma site hernias. Am Surg. Dec. 2005;71(12):1047-50.

Kridel et al., Septal perforation repair with acellular human dermal allograft. Arch Otolaryngol Head Neck Surg. Jan. 1998;124(1):73-8.

Laidlaw et al., Tympanic membrane repair with a dermal allograft. Laryngoscope. Apr. 2001;111(4 Pt 1):702-7.

Lee et al., In vitro evaluation of a poly(lactide-co-glycolide)-collagen composite scaffold for bone regeneration. Biomaterials. Jun. 2006;27(18):3466-72.

Lu et al., Novel porous aortic elastin and collagen scaffolds for tissue engineering. Biomaterials. Oct. 2004;25(22):5227-37.

Reihsner et al., Biomechanical properties of elastase treated palmar aponeuroses. Connect Tissue Res. 1991;26(1-2):77-86.

Simon et al., Early failure of the tissue engineered porcine heart valve SYNERGRAFT in pediatric patients. Eur J Cardiothorac Surg. Jun. 2003;23(6):1002-6.

Stella et al., On the biomechanical function of scaffolds for engineering load-bearing soft tissues. Acta Biomater. Jul. 2010;6(7):2365-81.

Tedder et al., Stabilized collagen scaffolds for heart valve tissue engineering. Tissue Eng Part A. Jun. 2009;15(6):1257-68.

Xu et al., A Porcine-Derived Acellular Dermal Scaffold that Supports Soft Tissue Regeneration: Removal of Terminal Galactose-alpha-(1,3)-Galactose and Retention of Matrix Structure. Tissue Engineering: Part A. Jul. 2009;15(7):1807-1819.

Yuan et al., Effects of collagenase and elastase on the mechanical properties of lung tissue strips. J Appl Physiol (1985). Jul. 2000;89(1):3-14.

Zheng et al., Porcine small intestine submucosa (SIS) is not an acellular collagenous matrix and contains porcine DNA: possible implications in human implantation. J Biomed Mater Res B Appl Biomater. Apr. 2005;73(1):61-7.

* cited by examiner

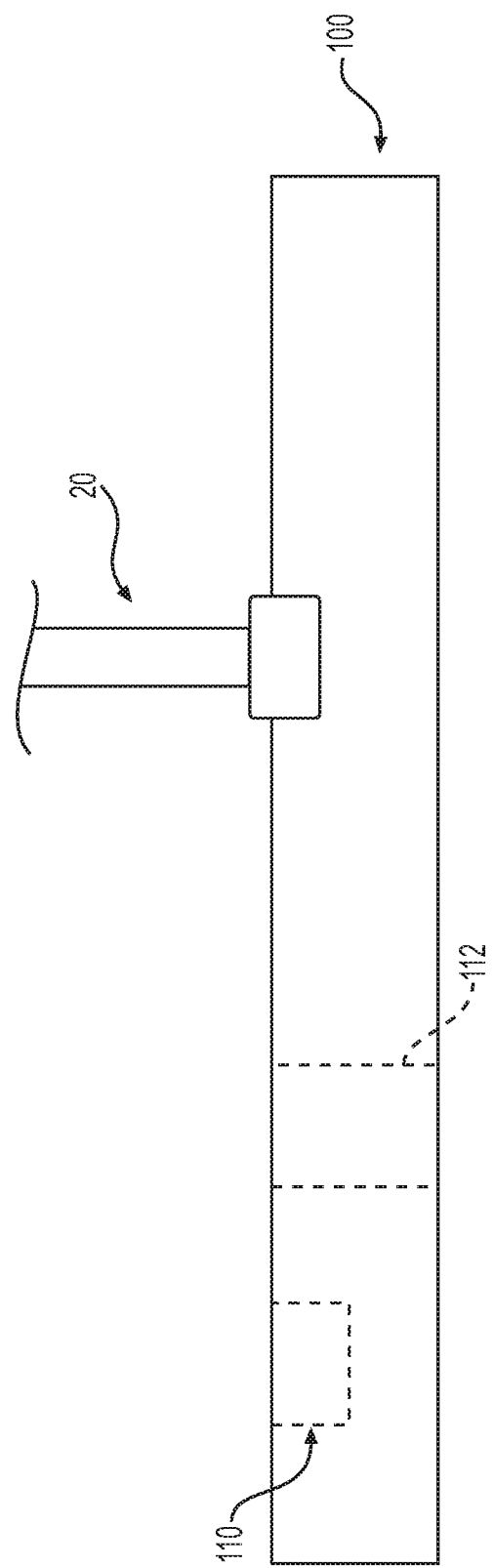

DEVICES AND METHODS FOR TISSUE CRYOMILLING

This application claims priority under 35 USC § 119 to U.S. Provisional Application No. 62/438,241, which was filed on Dec. 22, 2016, and is herein incorporated by referenced in its entirety.

The present disclosure relates to methods for processing tissue, including tissue matrices. The methods allow for improved machining of tissues to alter shapes, improve various features, produce particulates, and/or create new features such as holes.

Various tissue-derived products are used to regenerate, repair, or otherwise treat diseased or damaged tissues and organs. Such products can include intact tissue grafts or acellular or reconstituted acellular tissues (e.g., acellular tissue matrices from skin, intestine, or other tissues, with or without cell seeding). Such products generally have mechanical properties determined by the tissue source (i.e., tissue type and animal from which it originated) and the processing parameters used to produce the tissue products.

Desirable tissue products, such as acellular tissue matrices, may require certain features relating, for example, to their shape, surface texture, presence of holes or openings, and surface regularity. Machining, or otherwise processing tissues to improve or alter the shape or other features, however, can present various challenges. For example, soft tissue presents challenges when trying to produce sheets or other configurations having repeatable and uniform dimensions (e.g., thicknesses) or surface textures. In addition, formation of holes or openings in tissue products having repeatable and consistent shapes and positions can be difficult. In addition, machining soft tissue products to produce particulates with desired uniformity of shape or size can be challenging.

Accordingly, the present application provides improved methods for processing tissues to modify or control the tissue shapes, dimensions, surface features, presence of holes or openings, or other physical characteristics that may be modified by mechanical processing. The methods and devices can also be used to machine tissue or tissue products to produce particulate tissues with a desired size, size distribution, and/or uniformity.

According to various embodiments, a method for processing tissue products is provided. The method can include selecting a soft tissue product, and contacting the soft tissue product with a support surface, wherein the support surface comprises a group of openings, and wherein the soft tissue product covers at least some of the openings. The method can further comprise creating a negative pressure through at least some of the openings to remove fluid or air that may be present between the soft tissue product and the support surface, cooling the soft tissue product while in contact with the support surface to freeze the soft tissue product, and contacting the soft tissue product with a cutting instrument while the soft tissue product is frozen.

According to other embodiments, a device for processing soft tissue products is provided. The device can include a support surface, wherein the support surface comprises a group of openings passing through the support surface, and a negative pressure source in fluid communication with the group of openings to allow negative pressure to be applied through the openings when a soft tissue product is in contact with the support surface. The device can also include a cooling system near or in contact with the support surface to allow cooling of the support surface to a temperature of about −80° C. to −30° C.; and a cutting instrument movable to a position near the support surface and capable of being horizontally translated over the support surface to machine a soft tissue product in contact with the support surface.

DESCRIPTION OF THE DRAWINGS

FIG. 5 illustrates a side view of a tissue product with certain features that can be produced using the various embodiments of the present methods and devices.

DESCRIPTION OF CERTAIN EXEMPLARY EMBODIMENTS

Reference will now be made in detail to certain exemplary embodiments according to the present disclosure, certain examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including," as well as other forms, such as "includes" and "included," is not limiting. Any range described herein will be understood to include the endpoints and all values between the endpoints.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

Various human and animal tissues can be used to produce products for treating patients. For example, various tissue products for regeneration, repair, augmentation, reinforcement, and/or treatment of human tissues that have been damaged or lost due to various diseases and/or structural damage (e.g., from trauma, surgery, atrophy, and/or long-term wear and degeneration) have been produced. Such products can include, for example, acellular tissue matrices, processed tissue matrices (e.g., tissue matrices made into particulate, sponge-like, or composite forms), tissue allografts or xenografts, and/or reconstituted tissues (i.e., at least partially decellularized tissues that have been seeded with cells to produce viable materials).

The presently disclosed methods and devices can be used to process a variety of different tissues or tissue products. For example, the presently disclosed methods and devices can be used to machine, shape, or otherwise alter the physical form of any soft tissue or any tissue product derived from soft tissue, including, for example, acellular tissue matrices, partially decellularized tissues, composite tissue matrices, reconstituted tissues, tissue allograft, autografts, or xenografts. Furthermore, the presently disclosed methods and devices can be used during formation of tissue products such as acellular tissue matrices or to modify already formed tissue matrices or other tissue products. In addition, the presently disclosed methods and devices can be used to produce particulate materials from tissue products.

Figure 1:
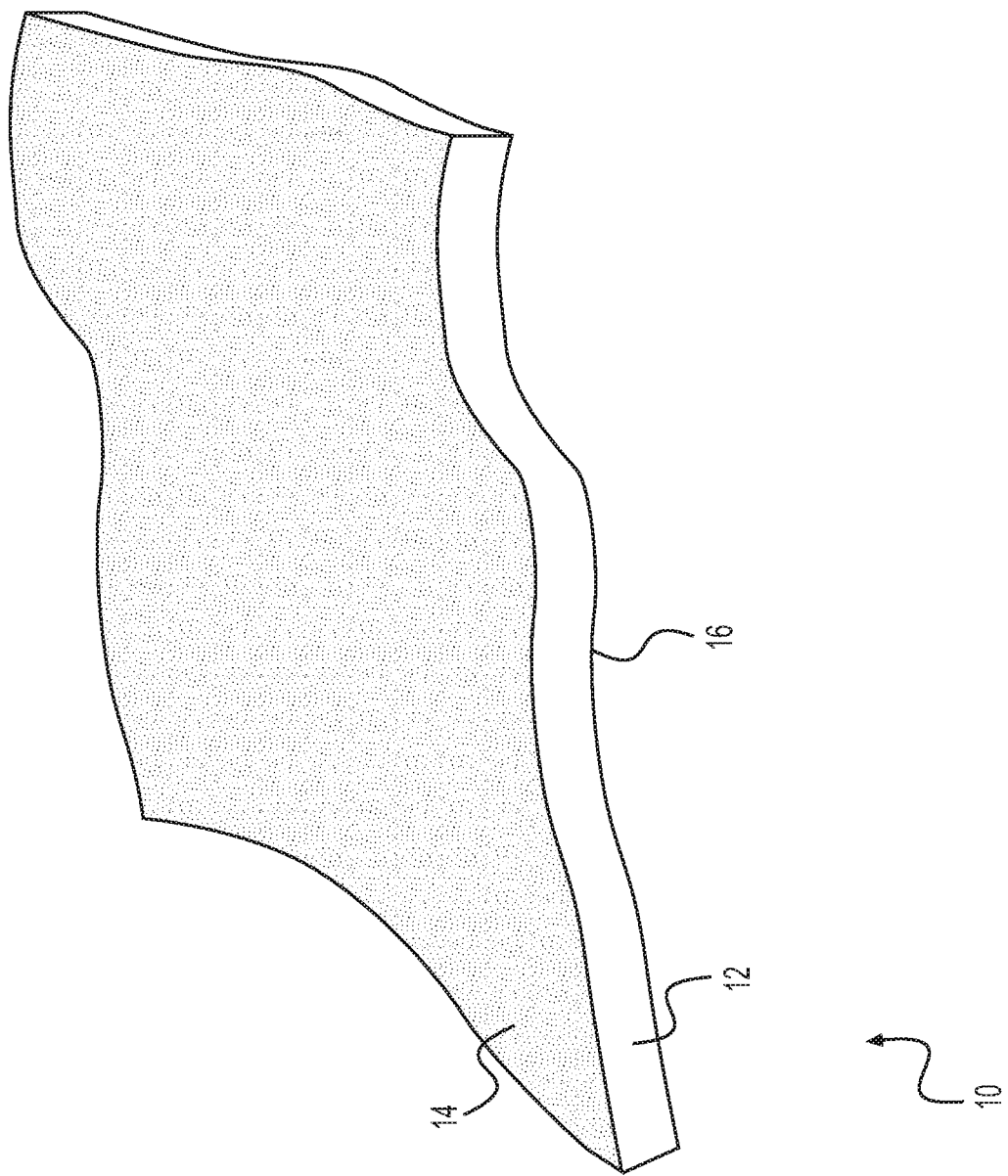
FIG. 1 provides a perspective view of a tissue product that may be processed using various embodiments of the present methods and devices.

By way of example, FIG. 1 provides a perspective view of a tissue product 10 that may be processed using various embodiments of the present methods and devices. As shown, the tissue product 10 includes a sheet of soft-tissue or soft-tissue derived material having a main body 12 with a top surface 14 and bottom surface 16. The tissue product 10 could include, for example, a sheet of unprocessed or partially processed intact tissue (e.g., skin, dermis, stomach, adipose) or a sheet of acellular tissue matrix, such as ALLODERM® or STRATTICE™, acellular dermal tissue matrices produced by LIFECELL CORPORATION, Branchburg, N.J., or similar acellular tissue matrix products.

Although FIG. 1 illustrates a sheet of tissue, the present methods and devices can be used to process tissues in any suitable shape or form. For example, the tissue to be processed can be a bulk, irregular, or regularly-shaped geometric form, such as a mass of irregular tissue, or a tissue in the form of a cube, sphere, tube, cylinder, or other shape.

Figure 2:
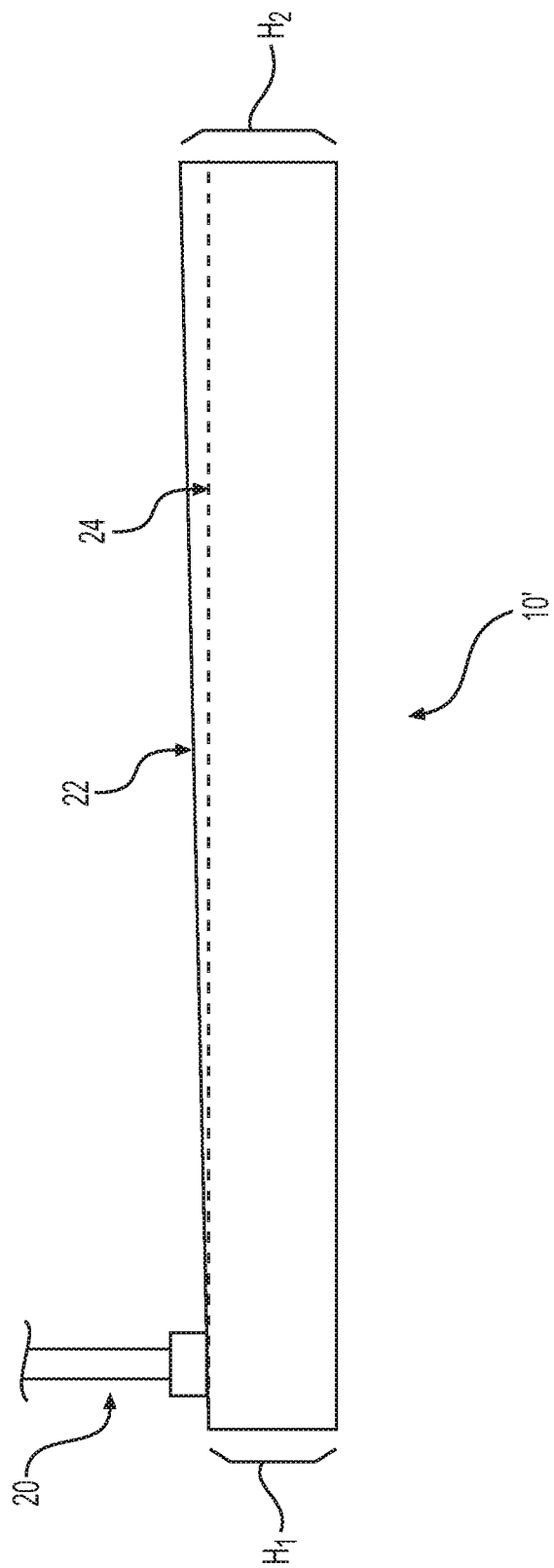
FIG. 2 is a side end view of a tissue product that may be processed using various embodiments of the present methods and devices.

Those who work with tissue products, including allografts, autografts, xenografts, or processed tissues such as acellular tissue matrices, will appreciate that source tissues, i.e., the original tissue that is harvested from a human or animal before final processing, may have natural variations in dimensions (e.g., in thickness) due to variations in anatomic source sites, variation in animal or human source, and variations and inconsistencies in harvesting techniques. For example, FIG. 2 is a side end view of a tissue product 10' that may be processed using various embodiments of the present methods and devices. The tissue product 10' is illustrated as a sheet, which may be formed from dermis or other sheet-like tissues, such as intestinal components, or tissue cut into sheet forms. As shown, the tissue has a variation in heights H1 and H2, across its width or length, which may develop during harvesting or be caused by anatomic variations. As illustrated in FIG. 2, the cutting tool 20 can be used to remove the irregular surface 22, resulting in a tissue product 10' with a more uniform height, defined, in part, by new surface 24.

Generally, dimension variations within a single tissue product, such as the varying heights of unprocessed tissue product 10' of FIG. 2, or variations between multiple tissue products belonging to a single commercial line, may be undesirable. For example, variations between multiple tissue products may lead to inconsistent mechanical properties or tissue volumes when implanted. In addition, surgeons will generally prefer consistent mechanical feel and handling. Accordingly, as discussed further below, the present application provides methods and devices where a cutting instrument can be used to modify a tissue product.

As mentioned above, soft tissues can be cut or otherwise modified to produce desired shapes, surface features, or other physical changes (e.g., holes, particulates). Producing such modifications, however, may present challenges, especially when a high level of precision and/or consistency is desired. Accordingly, the present application provides devices and methods to allow a high level of precision or consistency without otherwise damaging tissues.

The methods for processing tissue can include several steps that allow secure fixation of the tissue, precision or accuracy in processing, modification of the physical properties of the tissue to facilitate cutting (e.g., by freezing the tissue to produce a machineable solid material), and final machining or cutting of the tissue.

According to various embodiments, a method for processing tissue products is provided. The method can include selecting a soft tissue product and contacting the soft tissue product with a support surface, wherein the support surface comprises a group of openings, and wherein the soft tissue product covers at least some of the openings. The method can further comprise creating a negative pressure through at least some of the openings to remove fluid or air that may be present between the soft tissue product and the support surface, cooling the soft tissue product while in contact with the support surface to freeze the soft tissue product, and contacting the soft tissue product with a cutting instrument while the soft tissue product is frozen.

According to other embodiments, a device for processing soft tissue products is provided. The device can include a support surface, wherein the support surface comprises a group of openings passing through the surface, and a negative pressure source in fluid communication with the group of openings to allow negative pressure to be applied through the openings when a soft tissue product is in contact with the support surface. The device can also include a cooling system near or in contact with the support surface to allow cooling of the support surface to a temperature of about −80° C. to −30° C.; and a cutting instrument movable to a position near the support surface and capable of being horizontally translated over the support surface to machine a soft tissue product in contact with the support surface.

As noted, the cutting instrument can be configured to be horizontally translated over the support surface. It should be appreciated, however, that the cutting instrument may also move in other directions (i.e., vertically), to allow formation of vertically oriented structures (e.g., holes), or to allow formation of desired 3-D shapes (e.g., to produce a surface configuration, produce a shape such as a cube, column, tube, or other structure that may desirably be machined). Accordingly, in some embodiments, the cutting instrument is vertically mobile or both horizontally and vertically translatable either simultaneously or separately.

Figure 3:
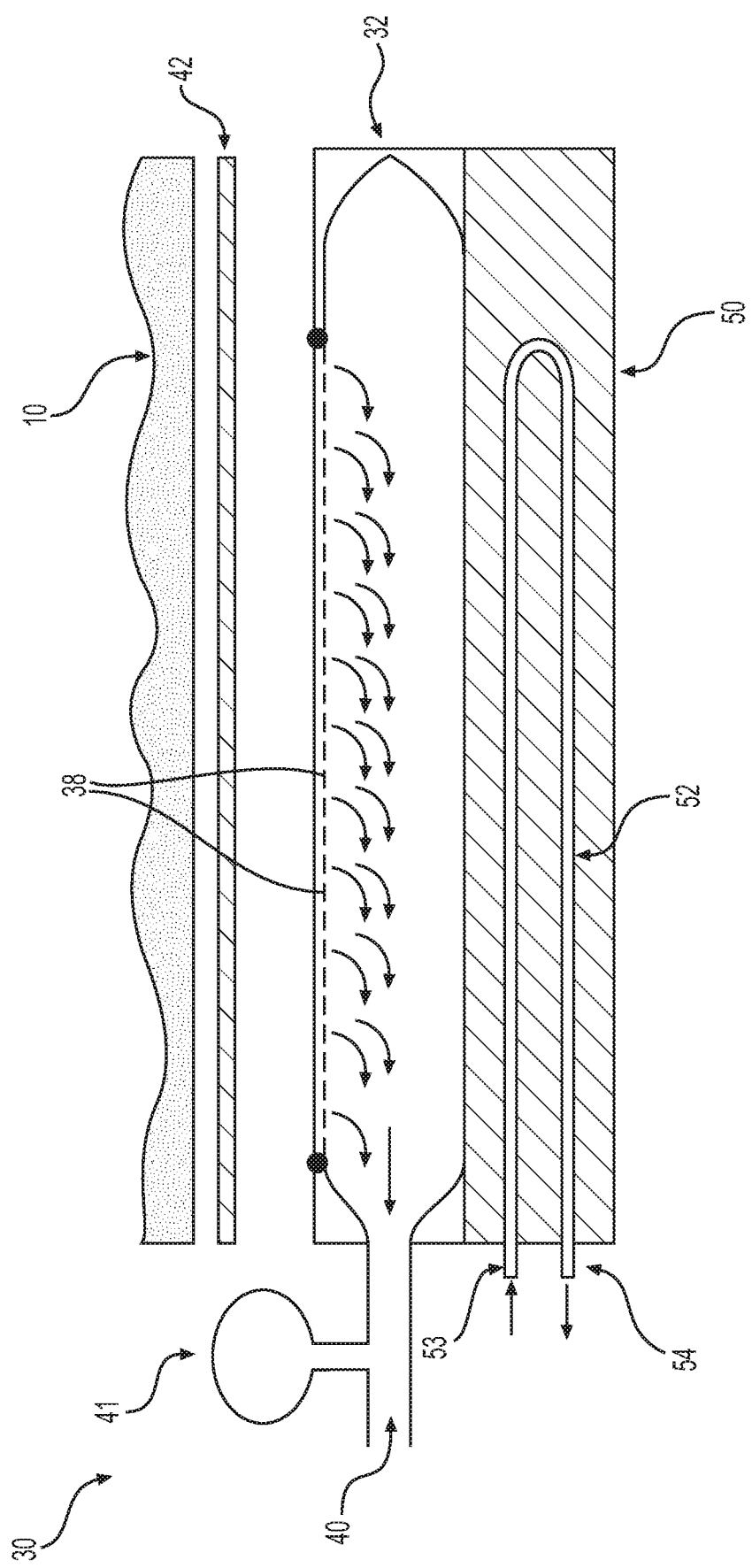
FIG. 3 is a side view of a device for processing tissue products according to various embodiments of the present methods and devices.

FIGS. 3, 4A-4C, 5, and 6A-6B further illustrate the methods and devices discussed herein. FIG. 3 is a side view of a device 30 for processing tissue products according to various embodiments. As shown, the device 30 includes a support surface 32, which may include a group of openings 38 passing therethrough. The device 30 further includes a negative pressure source 40 to produce negative pressure, e.g., suction, through the openings, thereby securing a tissue product 10 to the surface. The device 30 includes a cooling system 50 in contact with the support surface 32 to allow cooling and freezing of the tissue product 10 prior to cutting or machining with a cutting instrument 20.

The device 30 is now described in more detail. As mentioned above, the device 30 can include a support surface 32 to hold a tissue 10 in place during processing. Generally, the support surface 32 will include a flat, rigid support, such as an aluminum, stainless steel, rigid polymeric, ceramic, or other support material that can incorporate openings 38. Further, the support surface 32 may be formed of a material that is readily sterilizable or easily cleaned, and is thermally conductive to facilitate heat transfer and cooling of tissue product 10, as discussed in further detail below.

In some cases, the support surface 32 can be formed of materials that can be made perfectly flat (or have other desired configurations) at the temperature for tissue processing. For example, if the tissue product is to be machined at cryogenic temperatures, it may be desirable to achieve flatness of the support surface 32 at the selected cryogenic temperature. But a support surface that is flat at room temperature may warp out of plane at cryogenic operating temperatures.

Thus, it can be advantageous to use a support material that can be easily machined at cryogenic operating temperatures to impart the perfect flatness at tissue processing temperatures. Aluminum can be machined at cryogenic temperatures, whereas stainless steels become increasingly difficult to machine at colder temperatures. Accordingly, the support may be formed of aluminum or any material that can be machined to a desired shape or configuration at tissue processing temperatures.

Figure 4A:
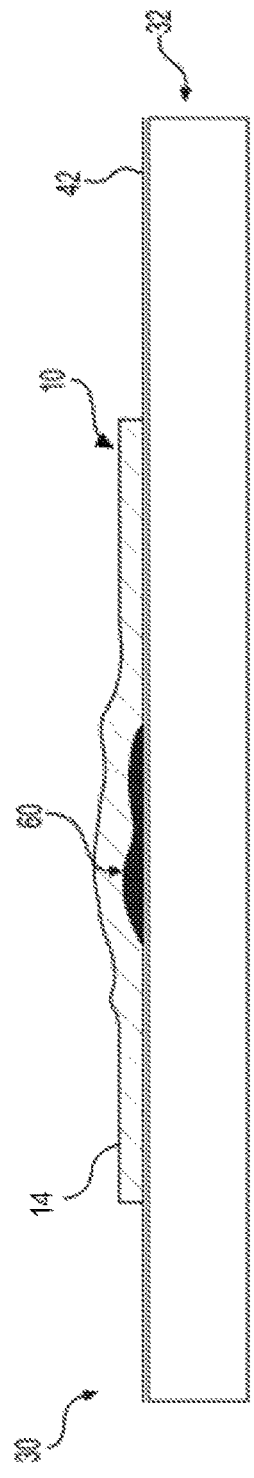
FIG. 4A illustrates a step in a process for processing tissue products according to various embodiments of the present methods and devices.
Figure 4B:
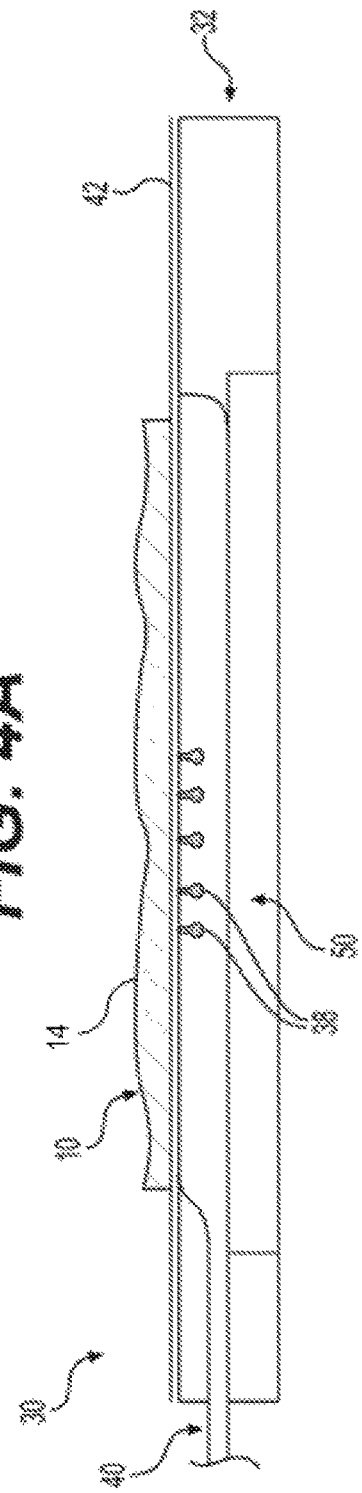
FIG. 4B illustrates another step in a process for processing tissue products according to various embodiments of the present methods and devices.
Figure 4C:
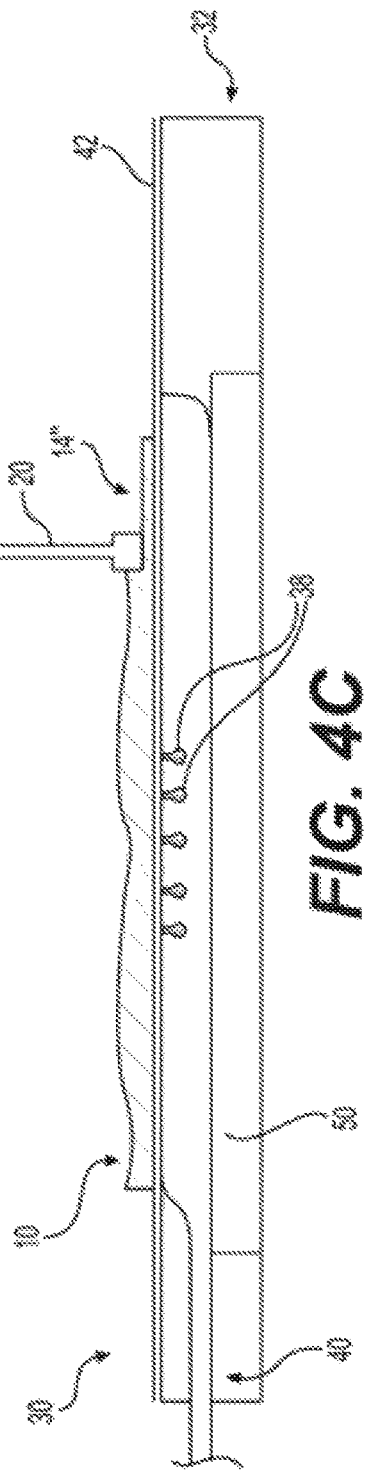
FIG. 4C illustrates another step in a process for processing tissue products according to various embodiments of the present methods and devices.

The support surface 32 may optionally include a second material 42 (shown separated from the support surface 32 in FIG. 3, but necessarily in contact with the support surface 32 and material 10 when in use, as shown in FIGS. 4A-4C). The second material 42 can include a sheet, e.g., a flexible sheet, which may serve a number of purposes. The material 42 can be disposable, and may be sterile, thereby reducing the need to clean or sterilize the support surface 32. The second material 42 can also be formed of a material that will not adhere to the tissue product 10 when cooled. The second material 42 can be formed of a porous material, such as TYVEK® (spun polypropylene), or other suitable material.

As used herein, the second material 42 is considered part of the support 32 during use, and the second material 42 can include macroscopic openings or sufficient porosity to allow suction to pass through from the support 32. Accordingly, it should be understood that placing the tissue product 10 in contact with the support 32 can mean placing the tissue product 10 directly in contact with the support 32 or placing the tissue product in contact with the second material 42

The device 30 also includes a negative pressure source 40 for providing negative pressure or suction through the openings 38 in the support surface 32. The negative pressure source 40 can include a typical vacuum source with a pressure control system 41. Generally, the pressure generated by the negative pressure source 40 need only remove excess fluids and secure the tissue product 10 in place on support surface 32. For example, tissue product 10 could be subject to 1, 2, 3, 4, 5, 10, 20, or 30 psi. In certain embodiments, the pressure is at least 3 psi.

The device 30 also includes a cooling system 50 for cooling a tissue product 10 in contact with the support surface 32 or second material 42. A variety of suitable cooling systems may be used, but exemplary systems can include a conduit(s) 52, an inlet 53, and an outlet 54 for the passage of cooling fluids through cooling system 50. Cooling system 50 may be provided with a variety of fluid flow paths, fluid flow rates, coolant types, and other physical or operational characteristics, based on the desired rate and degree of cooling. Any suitable cooling fluid, including liquid nitrogen or cooled silicone, can be used.

FIG. 4A-4C illustrate steps for processing tissue product 10 using the device 30, or variations thereof. As illustrated in FIG. 4A, the method of processing tissue can include placing a selected tissue 10 on a support surface 32 of the device 30 (including the solid support 32 with or without second material 42). Since the tissue can include a flexible soft-tissue product, such as a sheet, the tissue may not lie completely flat or without small or sizable gaps 60 (e.g., air pockets, residual liquid, or small folds may exist) between the tissue 10 and support surface 32. Accordingly, in order to remove air pockets or other spaces such as fluid 60 between the tissue 10 and support surface 32, the negative pressure source 40 is engaged, thereby sucking air and fluid from between the tissue 10 and support 32, through openings 38 in the support and securing tissue 10 to support surface 32, as shown in FIG. 4B.

As noted above, the tissue product 10 can also be frozen to make it more suitable for machining or cutting. Accordingly, the tissue product 10, while in contact with the support 32, can be cooled, thereby freezing the tissue product 10 to produce a more solid and rigid tissue. A solid or rigid tissue will be more readily cut, or otherwise machined, to produce a desired surface or shape (e.g., by leveling, smoothing, or otherwise modifying the surface, or by producing shapes or holes/openings in the surface), or particulate configuration.

The tissue product 10 can be cooled and frozen via the cooling system 50 that is in contact with or near the support surface 32. The cooling system 50 need not be in physical direct contact with the support surface 32, but may simply be close enough to or otherwise configured to provide thermal contact (i.e., to allow cooling of the tissue).

The cooling system 50 and use of negative pressure source 40 can be implemented in a number of ways. For example, in one embodiment, the negative pressure source 40 is engaged to remove spaces 60 (e.g., air or fluids) and secure the tissue 10 to the support surface 32 before any cooling is provided by the cooling system 50. In another embodiment, the cooling system 50 is used to cool the support surface 32 prior to placement of the tissue 10 on the support surface 32. This allows tissue 10 to be cooled and exposed to negative pressure source 40 simultaneously.

The degree of cooling and rate of cooling may be selected based on the tissue to be processed, the type of subsequent machine processing, and desired rate of cooling. Generally, the temperature of support surface 32 should be below the glass transition or freezing temperature of the tissue product 10, such that the heat generated from machining the tissue product 10 does not raise the temperature of the tissue product 10 above its glass transition or freezing temperature. In an exemplary embodiment, the support surface is maintained between 5° C. and 10° C. degrees below the glass transition or freezing point of the tissue product 10 to adequately to remove the heat generated during machining of the tissue product 10 and keep the tissue product 10 solid. However, it may be advantageous to decrease the temperature of the support surface 32 even further (e.g., −30° C. to −80° C.) in order to remove heat generated during machining more quickly. Further, cooling the support surface 32 sufficiently can allow for a shorter preparation time (i.e., initial freezing of the tissue) as well as more rapid extraction of machining heat. As discussed above, the system 30 may be configured to cool the tissue to between −30° C. and −80° C., but for tissues that have higher or lower freezing or glass transition temperatures, which may be altered by the presence of storage or processing fluids, the temperature may be appropriately altered.

The specific cutting instrument 20 can be selected based on the type of machining being performed and desired final product or particulate configuration. For example, end mills, where the axis of tool rotation is perpendicular to the tissue plane, and horizontal mills, where the axis of tool rotation is parallel to the tissue plane (like a wood planer), can be used. The cutting instrument can include a fly cutter, an end mill having anywhere between one and six flutes, a shell cutter, or a face mill. In addition, drills, ball end mills, and slitting saws may be used to impart other surface features such as holes, divots, or slots within the tissue.

Once secured and frozen, the tissue product 10 can be machined or processed with the cutting instrument 20. For example, as shown in FIG. 4C, the instrument 20 may be moved across the top surface 14, thereby removing material and producing an altered top surface 14". Alternatively, the cutting instrument can be used to produce other features, shapes, or changes, as discussed herein.

Figure 6A:
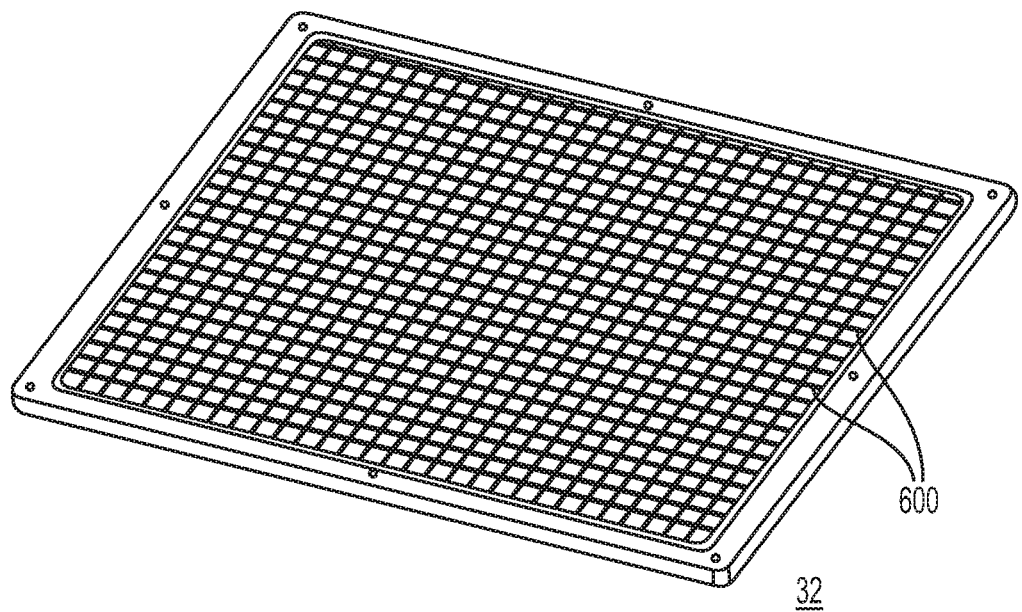
FIG. 6A is a perspective view of a support surface that may be incorporated with the presently disclosed devices and methods.
Figure 6B:
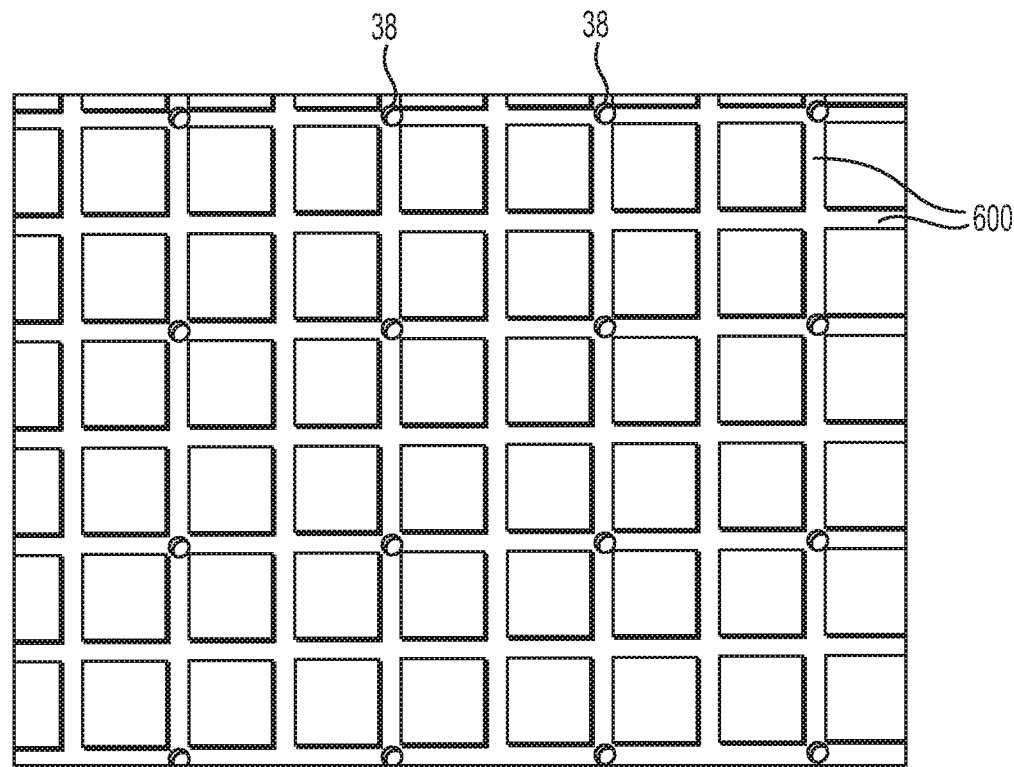
FIG. 6B is an enlarged top view of a portion of the support surface of FIG. 6A.

Other variations to the device 30 may be made. For example, FIG. 6A is a perspective view of a support surface 32 that may be incorporated with the presently disclosed devices and methods. FIG. 6B is an enlarged top view of a portion of the support surface of FIG. 6A. As shown, the support surface 32 includes grooves 600 or channels, which can facilitate rapid or complete removal of fluids within the tissue product 10. In such an embodiment, the openings 38 can be positioned within the grooves 600 or within and outside the grooves The devices and methods discussed herein can be used to produce a variety of different machining or processing results. For example, as discussed previously, the devices and methods can be used to control or alter a tissue surface, by, for example, changing tissue product thickness, improving or altering surface uniformity, or forming surface modifications (e.g., grooves, channels, holes, divots, pilot holes) or other features. For example, FIG. 5 illustrates a side view of a tissue product 100 with certain features that can be produced using the various embodiments of the present methods and devices. As shown, the cutting instrument 20 is used to form a hole 112 or pilot hole 110 (i.e., a hole passing part way through the product).

The devices and methods can also or alternatively be used to make desired shapes, including, for example, sheets with particular shapes (e.g., circle, crescent, crescent-line, square, rectangular, or any other geometric shape), 3-D shapes (spheres, rods or other shapes), or irregular custom forms to mimic a particular anatomic site.

In some embodiments, the devices and methods can be used to produce tissue products that are cylindrical, or similar to cylindrical (e.g., a tapered or irregular cylindrical structure) in shape. For example, cylindrical tissue products can be used as tissue treatment materials to fill voids such as fistulas, tunneling wounds, or other structures. In addition, cylindrical shapes may be used as components of other tissue treatment devices, e.g., to form braided and/or multi-component materials for tendon or ligament treatment, to form slings or other structure (e.g., for bladder or other genitourinary treatment), or as support structures for breast (e.g., for mastopexy) or other tissues.

Figure 7:
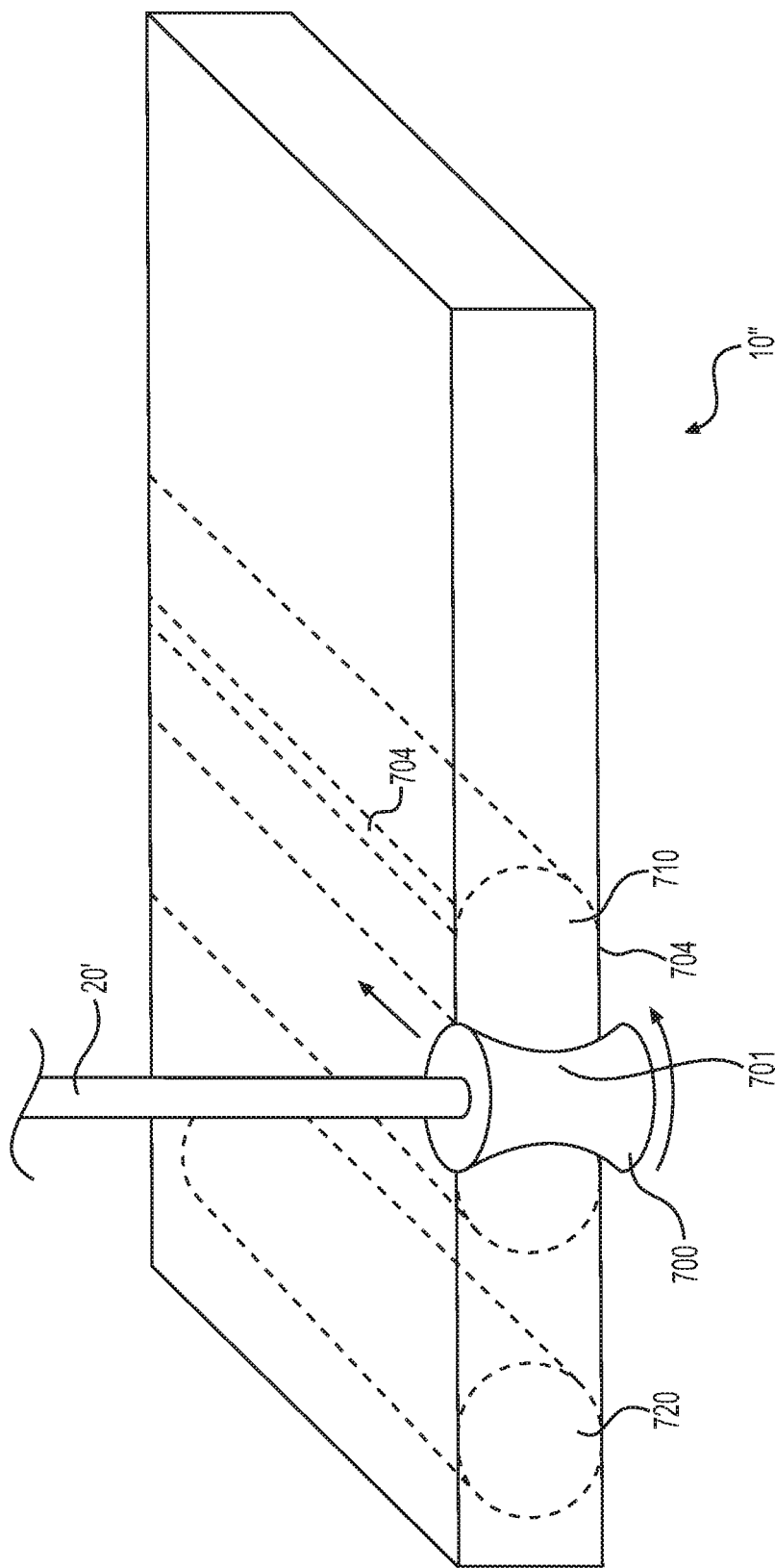
FIG. 7 illustrates a process used to produce various shapes for tissues products according to embodiments of the present devices and methods.

A process for producing a cylindrical tissue product is illustrated in FIG. 7. As shown, a tissue 10", which can include a sheet or other form, can be secured and frozen as discussed above. But, according to FIG. 7, an instrument 20' having a specially shaped cutting head 700 can be used. The head 700 can include a curved surface 701 that can be passed through the tissue 10" while rotating or otherwise moving to effect cutting on opposite sides of a cutting site 710, thereby removing tissue to leave a substantially cylindrical form 720 (shown as an exemplary shape left after cutting on two sides of a site 710).

It will be understood that the cylindrical form may not be perfectly mathematically cylindrical (e.g., may have flat top or bottom edges 704 or may be tapered along its length). Additionally, tissue products disclosed herein may intentionally include surface variations to facilitate various functions such as complete site filling, securing the material via friction or pressure, or providing a site for passage of sutures or other fixation means.

It will also be appreciated that variations of the cutting head and cutting path can be used to form other shapes including spheres, materials with channels or opening, notches, barbs, or other features.

As mentioned above, the processes and devices discussed herein, rather than being used to alter the shape or configuration of the tissue product 10, may be used to create particles of the tissue product 10. Using the disclosed methods and devices, the particles can be formed with a desired degree of uniformity in terms of size and/or shape. For example, simply milling a tissue in bulk form can result in a wide distribution of sizes and shapes, which may be undesirable for some applications. In contrast, the disclosed processing devices and methods including freezing and securing the tissue product can allow production of tissue matrix or other tissue particulates with uniformity of size and shape (e.g., within a desired size distribution or shape distribution). As such, the process can prevent or reduce the need for further particulate processing such as filtering or other separation in order to produce the desired sizes and shapes.

The devices and methods discussed herein can be used to process a variety of tissue product types and configurations. For example, any suitable soft tissue or material derived from soft tissue can be processed. The materials to be processed can be in the form of a sheet or a mass (e.g., block, irregular soft tissue mass). The tissue can be skin, can be derived from skin (e.g., dermis) or can be derived from other soft tissues such adipose tissue, muscle, pericardium, nerve tissue, intestinal tissue, dura, bladder, stomach, fascia, tendon, ligament, lung, liver, pancreas, or kidney. In addition, the products to be processed can include materials similar to tissue, but not necessarily tissue, including, collagenous products, synthetics, composite materials, or silk. Although described for soft tissues, the devices and methods may be used for cartilaginous or bony tissues. "Tissue products" will be understood to refer to any of the aforementioned tissues or tissue-derived products.

The invention claimed is:

1. A method for processing tissue products, comprising:
   selecting a soft tissue product;
   contacting the soft tissue product with a support surface, wherein the support surface comprises a group of openings, and wherein the soft tissue product covers at least some of the openings;
   creating a negative pressure through at least some of the openings to remove fluid or air that may be present between the soft tissue product and the support surface;
   cooling the soft tissue product while in contact with the support surface to a temperature below the glass transition temperature of the soft tissue product to freeze the soft tissue product; and contacting the soft tissue product with a cutting instrument while the soft tissue product is frozen.

2. The method of claim 1, wherein the soft tissue product comprises a sheet.

3. The method of claim 1, wherein the soft tissue product comprises a product derived from at least one of adipose tissue, dermis, muscle, pericardium, nerve tissue, intestinal tissue, dura, bladder, stomach, fascia, tendon, ligament, lung, liver, pancreas, or kidney.

4. The method of claim 1, wherein the soft tissue product is a decellularized tissue product.

5. The method of claim 1, wherein cooling the tissue product comprises cooling the support surface.

6. The method of claim 5, wherein the support surface is cooled prior to contacting the soft tissue product with the support surface.

7. The method of claim 1, wherein the soft tissue product is cooled to a temperature between about −80° C. to −30° C.

8. The method of claim 1, wherein contacting the soft tissue product with a cutting instrument while the soft tissue product is frozen comprises contacting the tissue with a cutting blade to modify a thickness of the soft tissue product.

9. The method of claim 1, wherein contacting the soft tissue product with a cutting instrument while the soft tissue product is frozen comprises contacting the tissue with a cutting instrument to produce one or more openings partially or completely through the soft issue product.

10. The method of claim 1, wherein contacting the soft tissue product with a cutting instrument while the soft tissue product is frozen comprises contacting the tissue with a cutting blade to produce a more uniform thickness across the soft tissue product.

11. The method of claim 1, wherein contacting the soft tissue product with a cutting instrument while the soft tissue product is frozen comprises contacting the tissue with a curved cutting instrument to form a substantially cylindrically shaped tissue product.

12. The method of claim 1, wherein contacting the soft tissue product with a cutting instrument while the soft tissue product is frozen comprises contacting the tissue with a cutting blade to produce particulates having a desired degree of uniformity of at least one of size and shape.

13. The method of claim 1, wherein creating a negative pressure through at least some of the openings includes creating sufficient negative pressure to secure the soft tissue product to the support surface.

14. The method of claim 1, wherein the support surface comprises a rigid material covered with a semi-permeable material.

15. A tissue product produced using the method of claim 1.

16. A device for processing soft tissue products, comprising
   a support surface, wherein the support surface comprises a group of openings passing through the surface;
   a negative pressure source in fluid communication with the group of openings to allow negative pressure to be applied through the openings when a soft tissue product is in contact with the support surface;
   a cooling system near or in contact with the support surface to allow cooling of the support surface to a temperature of about −80° C. to −30° C.; and
   a cutting instrument movable to a position near the support surface and capable of being horizontally translated over the support surface to machine a soft tissue product in contact with the support surface.

17. The device of claim 16, wherein the cooling system includes a fluid supply conduit for passing cooling fluid near or in contact with the support surface.

18. The device of claim 16, wherein the cutting instrument comprises a cutting blade.

19. The device of claim 16 further comprising a system for controlling movement of the cutting instrument to maintain the cutting instrument at a substantially uniform distance from the support surface while moving the cutting instrument horizontally over the support surface.

20. The device of claim 16, wherein the support surface comprises a rigid material covered with a semi-permeable material.

* * * * *